United States Patent [19]  [11] 4,220,158
Delpy et al.  [45] Sep. 2, 1980

[54] TRANSCUTANEOUS PROBE

[75] Inventors: David T. Delpy; Dawood Parker, both of London, England

[73] Assignee: The Medishield Corporation Limited, London, England

[21] Appl. No.: 960,703

[22] Filed: Nov. 14, 1978

[30] Foreign Application Priority Data

Nov. 15, 1977 [GB] United Kingdom ............... 47434/77
May 31, 1978 [GB] United Kingdom ............... 25028/78

[51] Int. Cl.³ .............................................. A61B 5/00
[52] U.S. Cl. ................................ 128/632; 204/195 B; 204/195 P
[58] Field of Search ............................... 128/632, 635; 204/195 B, 195 P

[56] References Cited

U.S. PATENT DOCUMENTS

| | | | |
|---|---|---|---|
| 3,658,053 | 4/1972 | Fergusson et al. | 128/632 |
| 3,659,586 | 5/1972 | Johns et al. | 128/635 |
| 3,718,563 | 2/1973 | Krull et al. | 204/195 P |
| 3,767,552 | 10/1973 | Laver | 204/195 P |
| 3,869,354 | 3/1975 | Montalvo, Jr. | 204/195 B X |
| 3,979,274 | 9/1976 | Newman | 204/195 B |
| 4,005,700 | 2/1977 | Parker | 128/632 |

Primary Examiner—Lee S. Cohen
Attorney, Agent, or Firm—Dennison, Dennison, Meserole & Pollack

[57] ABSTRACT

A transcutaneous probe for causing oxygen and other gases or vapors carried in the bloodstream of a mammal to be extracted from the blood through the skin and passed to a device, such as a mass spectrometer, for analyzing the extracted gas. The probe has a boundary wall intended to be placed in contact with the skin comprising a first layer of gas permeable material and a second layer of perforate or porous gas-impermeable material in intimate contact with the first, the size and distribution of the perforations or pores in the second layer being such that the wall has a substantially uniform extrinsic macropermeability which is significantly lower than the inherent permeability of the first layer alone and such that in use, gas passes into the perforations or pores of the second layer from respective volumes of tissue which do not substantially overlap.

2 Claims, 2 Drawing Figures

TRANSCUTANEOUS PROBE

FIELD OF THE INVENTION

This invention relates to gas extraction devices of the type known as transcutaneous probes, which are non-invasive devices for causing oxygen and other gases or vapours (hereinafter referred to collectively as "gas") carried in the bloodstream of man (or other mammals) to be extracted from the blood through the skin and passed to a device (eg a mass spectrometer) for analysing the extracted gas.

BACKGROUND OF THE INVENTION

Examples of transcutaneous probes are described in "The Lancet" for May 3, 1975 (page 1016), United Kingdom patent specification No. 1,509,174 and United Kingdom patent application No. 28535/76. Such probes comprise a hollow body having a boundary wall intended to be placed on the skin, an internal chamber in which gas diffusing through the area of skin contacted by the boundary wall can be collected, heating means operable to heat that area of skin and an outlet from the collecting chamber through which the collected gas can be led away to an analysis instrument. Typically the boundary wall comprises a membrane of gas-permeable plastics supported in relation to the body of the probe by a member of gas-impermeable but porous material such that the extrinsic permeability of the wall is defined essentially by the plastics membrane. That is to say the porous supporting member is provided for the purpose of support only, and presents no significant impediment to the passage of gas which crosses the plastics membrane, into the collecting chamber.

One of the disadvantages of known gas-permeable membranes used in transcutaneous probes is that the material is hydrophilic. This has the consequence that the longer the membrane stays in contact with the skin of a patient the more moisture is absorbed in the material of the membrane, with a consequent reduction in its permeability. This leads to a non-uniform rate of extraction of gas through the skin.

This problem can be avoided by using a gas-permeable material, such as polytetrafluorethylene (PTFE), which is non-hydrophilic, but this suffers from the disadvantage that the inherent permeability of PTFE is too high. This results in oxygen and other gas being extracted from the bloodstream at too high a rate and consequently leads to the condition known as gas-depletion.

SUMMARY OF THE INVENTION

The present invention seeks to provide a form of construction for the boundary wall of a transcutaneous probe whereby these problems can be overcome or at least reduced and accordingly the invention resides in a transcutaneous probe of which the boundary wall comprises a first layer of gas-permeable material and a second layer of perforate or porous gas-impermeable material in intimate contact with the first, the size and distribution of the perforations or pores in the second layer being such that the wall has a substantially uniform extrinsic macropermeability which is significantly lower than the inherent permeability of the first layer alone, and preferably such that, in use, gas passes into the perforations or pores of the second layer from respective volumes of tissue which do not substantially overlap.

By the "extrinsic macropermeability" of the boundary wall is meant the permeability to gas passing into the probe's collecting chamber through that wall, as measured over the whole effective surface area of the wall.

A suitable relationship between the perforations or pores of the aforesaid second layer to achieve the desired characteristics is a separation of the perforations or pores by a distance at least three times their diameter.

In some embodiments of the invention the first layer of the boundary wall may be constituted by a membrane of gas-permeable plastics with the second layer being a perforate or porous member adapted to support the membrane in relation to the body of the probe, and the size and distribution of its perforations or pores being such as to achieve the aforesaid characteristics. Preferably, however, a composite membrane is employed comprising a first layer constituted by a gas-permeable plastics film and a second layer constituted by a perforate metal film with the composite membrane being supported in relation to the body of the probe by a further perforate or porous member the size and distribution of its perforations or pores being such as to have a negligible effect on the extrinsic macropermeability of the wall. It is in the latter form that the invention will now be more particularly described, by way of example, with reference to the accompanying drawings.

DESCRIPTION OF THE PREFERRED EMBODIMENT

Figure 1:
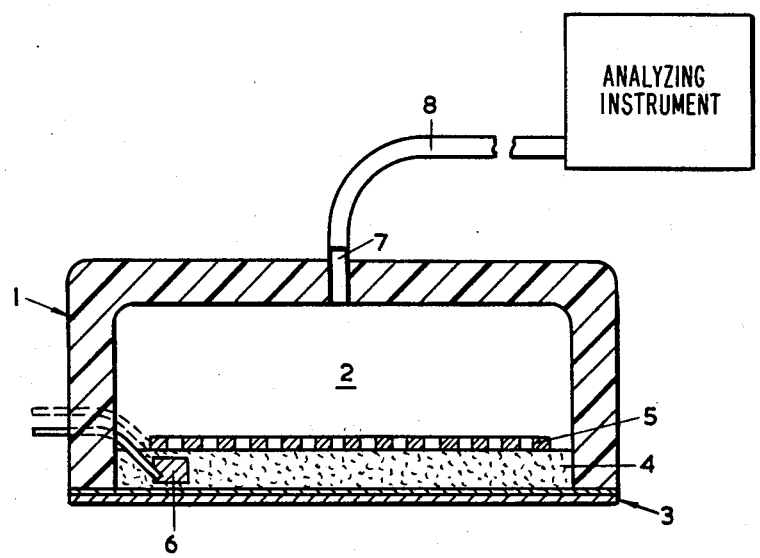
FIG. 1 is a diagrammatic cross section of one embodiment of a transcutaneous probe in accordance with the invention.

Referring to FIG. 1, the illustrated transcutaneous probe comprises a bowl shaped body 1 defining a gas collecting chamber 2 and having at its lower (as viewed) end a boundary wall comprising a composite membrane 3 supported by a porous member 4 made, for example, of sintered glass. The porosity of member 4 is of such a value as to have a negligible effect on the extrinsic macropermeability of the boundary wall, rather the permeability of the wall is defined essentially by the characteristics of the composite membrane 3.

The upper (as viewed) surface of the member 4 carries a heating element 5 by which the boundary wall and the adjacent area of a patient's skin can be heated in use of the probe, thereby to stimulate bloodflow in the capillaries in the vicinity of the device sufficient for the gas concentrations measured by the device to reasonably accurately reflect the gas concentrations in the arterial blood of the patient. In the illustrated embodiment the heater 5 comprises spiral strips of electro-resistive material as described in United Kingdom patent application No. 28535/76, the temperature of the boundary wall being monitored by means of an embedded thermister 6. However various other types and arrangements of heating means are known in the art, and may be employed instead. An outlet 7 is provided in the body of the probe through which the gases collected in the chamber 2 in use of the device can be led out of the chamber and through a conduit 8 to an analysing instrument 9 such as a mass spectrometer.

Figure 2:
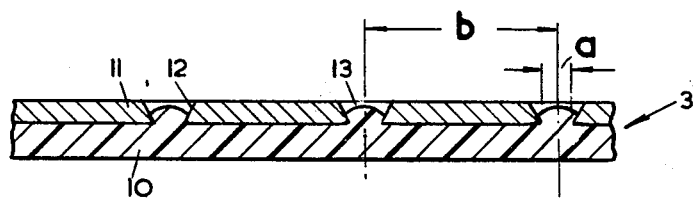
FIG. 2 shows the composite membrane of FIG. 1 on a larger scale.

Turning now to FIG. 2, the composite membrane 3 is shown to comprise a first layer of gas-permeable, plastics material 10 having a second layer of perforated metal 11 pressed into intimate contact with it. The material of the first layer is non-hydrophilic, and a preferred material is PTFE. The metal used in the second layer may be, for example, stainless steel or nickel.

The plastics film may be about 20-25 microns thick, while the metal film is about 20 microns thick.

Before the two layers are connected together, the metal layer 11 is provided with an array of very small holes 12 of circular transaxial cross section. In one preferred example the holes in the metal layer have a minimum diameter a of about 15 microns, and the centres of the holes are spaced apart by a distance b of about 85 microns. The holes 12 are usually produced by an etching process which results in the holes having a frustoconical form as illustrated. The metal layer is oriented relatively to the plastics layer 10 such that the smaller ends of the holes 12 are in contact with the respective major face of the plastics layer.

In order to ensure that the extrinsic macropermeability of the membrane is dictated by the size and distribution of the holes 12, it is important to ensure that the face of the metal layer 11 contacts the respective face of plastics layer 10 intimately. In one preferred method for ensuring this, the plastics layer is warmed overall and the two materials are then pressed firmly together. The degree of warming is such that a small amount of the plastics material becomes extruded through the tapered holes 12. Each blob 13 of plastics material so extruded tends to swell out on passing through the area of minimum cross section so that it acts as a key, preventing the two layers from separating from each other even in the absence of any adhesive between the two layers.

Alternatively, other methods could be used for producing a layer of metal in intimate contact with a layer of plastics material, and for forming the "grid" or other pattern of holes in the metal layer.

When either surface of the resultant membrane is placed in contact with the skin of a patient and a pressure differential established across it by reducing the pressure in the collecting chamber 2 of the probe, it has been found that the gas passing through each hole 12 into the collecting chamber tends to be drawn from a roughly hemispherical volume of skin and other tissue laying beneath the probe. The spacing of the holes 13 from each other is chosen so that these volumes of tissue from which the gas is extracted do not substantially overlap. This ensures that the gas entering each hole is drawn from a finite volume of tissue, and the rate of extraction of gas from this volume can be controlled, by means of the selected permeability of the membrane, at such a value that the problem of gas-depletion is reduced or minimised.

We claim:

1. A transcutaneous probe for measuring gas concentration in arterial blood including a body defining a gas collecting chamber, one wall portion of said chamber defined by a porous member and a composite membrane supported thereby, said composite membrane having a first layer constituted by a gas-permeable plastics film and a second layer constituted by a perforated metal film, the size and distribution of the perforations in the perforated metal film being such that the wall has a substantially uniform extrinsic macropermeability which is significantly lower than the inherent permeability of the first layer alone and that in use, gas passes into the perforations of said second layer from respective volumes of tissue which do not substantially overlap, each perforation in the perforated metal film having a frustoconical form, and the gas permeable plastics film being in intimate contact with the face of the perforated metal film which bears the smaller diameter ends of said perforations to prevent the first and second layers from separating from each other.

2. A transcutaneous probe according to claim 1 wherein portions of said plastics film extend into the perforations in the said metal film.

* * * * *